US00PP31365P2

(12) United States Plant Patent
Roberts

(10) Patent No.: US PP31,365 P2
(45) Date of Patent: Jan. 14, 2020

(54) ***CLEOME* PLANT NAMED 'CREME DE LA CREME'**

(50) Latin Name: *Cleome hassleriana*
Varietal Denomination: Creme de la Creme

(71) Applicant: Dan Laviana, Berlin, CT (US)

(72) Inventor: Christine Roberts, Winsted, CT (US)

(73) Assignee: Dan Laviana, Berlin, CT (US)

( * ) Notice: Subject to any disclaimer, the term of this patent is extended or adjusted under 35 U.S.C. 154(b) by 0 days.

(21) Appl. No.: 15/999,884

(22) Filed: Aug. 27, 2018

(51) Int. Cl.
*A01H 5/00* (2018.01)

(52) U.S. Cl.
USPC ..... Plt./416

(58) Field of Classification Search
USPC ..... Plt./416
CPC ..... A01H 5/00
See application file for complete search history.

(56) References Cited

PUBLICATIONS https://www.facebook.com/smalltowngardener/photos/creme-de-la-creme-cleome-super-new-from-sunny-border-nursery-typical-cleome-pink/1785752221496161/. Jan. 11, 2018.*

* cited by examiner

*Primary Examiner* — Annette H Para
(74) *Attorney, Agent, or Firm* — Penny J. Aguirre

(57) ABSTRACT

A new cultivar of *Cleome* plant, 'Creme de la Creme', that is characterized by its variegated foliage with leaflets that are green with margins that is creamy white in color, its flowers that fuchsia pink in color, its plant height of 60 to 91 cm, and its thick stems and have sharp spines at the base of the leaflets.

2 Drawing Sheets

Botanical classification: *Cleome hassleriana.*
Variety denomination: 'Creme de la Creme'.

BACKGROUND OF THE INVENTION

The present invention relates to a new and distinct cultivar of *Cleome hassleriana* and will be referred to hereafter by its cultivar name, 'Creme de la Creme'. 'Creme de la Creme' represents a new cultivar of *Cleome*, an annual grown for landscape use.

'Creme de la Creme' was discovered by the Inventor in June of 2016 as a naturally occurring meristematic mutation of a seedling grown from unnamed seeds of *Cleome hassleriana* that was growing in a field in Winsted, Conn.

Asexual propagation of the new cultivar was first accomplished by the Inventor by stem cuttings in Kensington, Conn. in June of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Creme de la Creme' as a unique cultivar of *Cleome.*

1. 'Creme de la Creme' exhibits variegated foliage with leaflets that are green with margins that is creamy white in color.
2. 'Creme de la Creme' exhibits flowers that fuchsia pink in color.
3. 'Creme de la Creme' exhibits a plant height of 60 to 91 cm.

4. 'Creme de la Creme' exhibits thick stems and have sharp spines at the base of the leaflets.

The parent plant of 'Creme de la Creme' differs from 'Creme de la Creme' in having all green, non-variegated foliage. 'Creme de la Creme' can be most closely compared to the *Cleome* seed strains 'Mauve Queen' (not patented) and 'Cherry Queen' (not patented). 'Mauve Queen' and 'Cherry Queen' are both similar to 'Creme de la Creme' in flower color, growth habit and leaf shape. 'Mauve Queen' and 'Cherry Queen' both differ from 'Creme de la Creme' in having non-variegated leaves and flower colors that varies. 'Creme de la Creme' can also be compared to the cultivar 'Robspidam' (U.S. Plant Pat. No. 15,933). 'Robspidam' is similar in flower color, but differs from 'Creme de la Creme' in having non-variegated foliage and larger inflorescences.

BRIEF DESCRIPTION OF THE DRAWINGS

The accompanying colored photographs illustrate the overall appearance and distinct characteristics of the new *Cleome* plant about 2 months in age as grown outdoors in plug trays in Kensington, Conn.

The photograph in FIG. 1 illustrates a number of plant in bloom of 'Creme de la Creme'.

Figure 1:
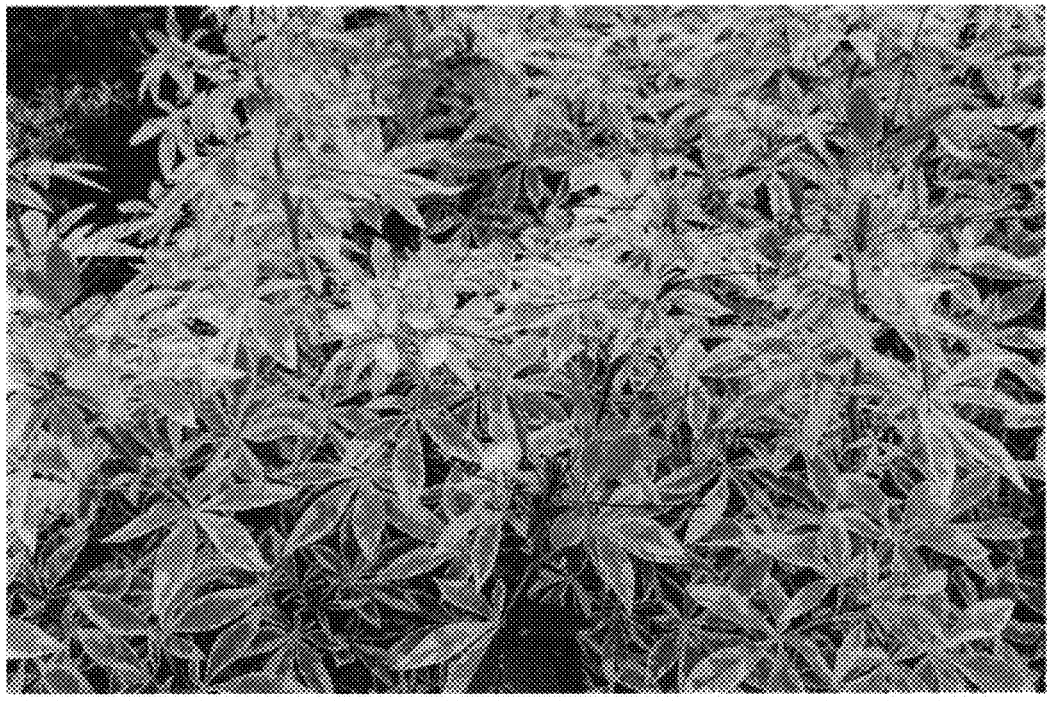
Figure 2:
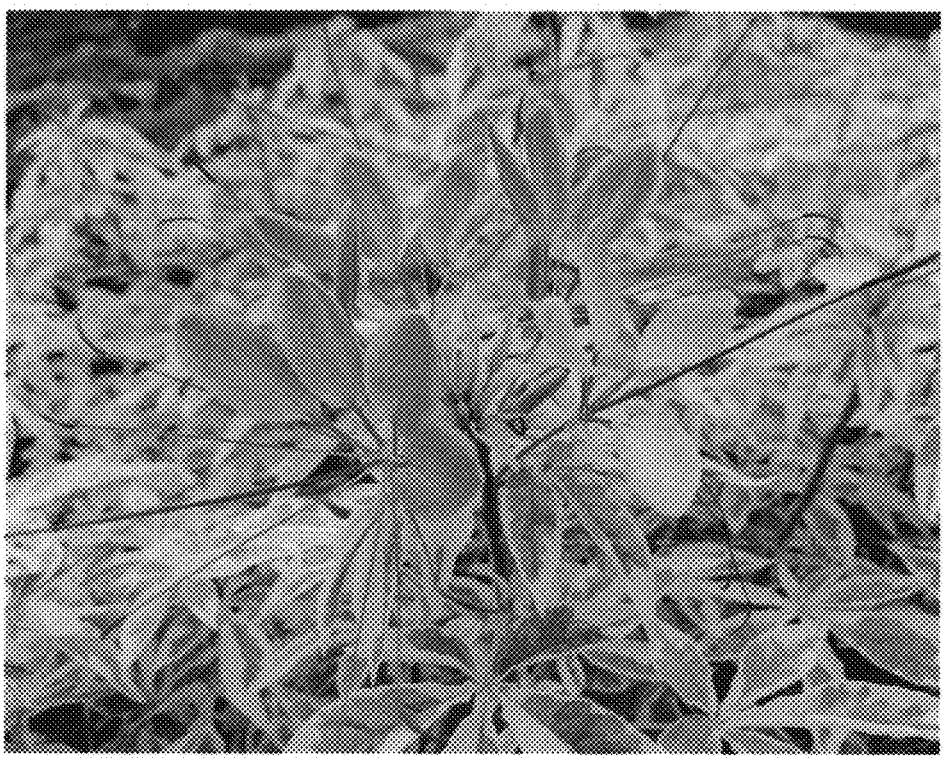

The photograph in FIG. 2 provides a close-up view of an inflorescence of 'Creme de la Creme'.

Figure 3:
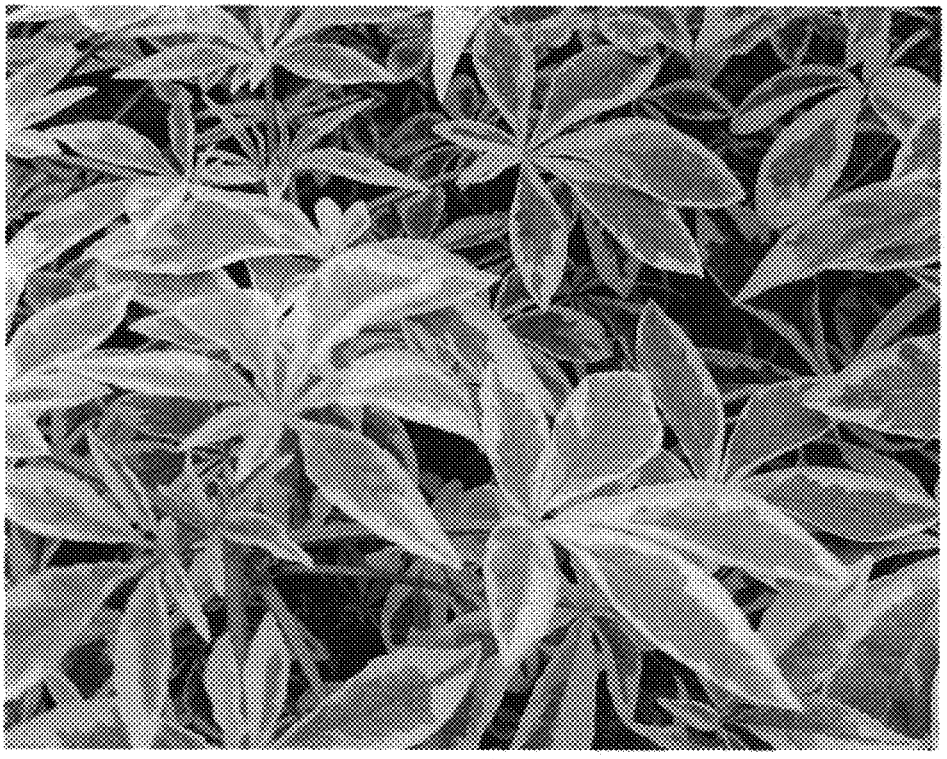

The photograph in FIG. 3 provides a close-up view of the foliage of 'Creme de la Creme'. The colors in the photograph may differ slightly from the color values cited in the detailed botanical description, which accurately describe the colors of the new *Cleome.*

DETAILED BOTANICAL DESCRIPTION

The following is a detailed description of the new cultivar as observed on 4-month-old plants of the new *Cleome* as grown outdoors in 5-inch containers in Kensington, Conn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Early summer to first frost in Kensington, Conn.

*Plant type.*—Annual.

*Plant habit.*—Upright and bushy.

*Height and spread.*—27 cm in height and 13 cm in spread on the potted plant used for data collection, mature height in a garden of 60 to 91 cm.

*Cold hardiness.*—Not hardy, grown as an annual.

*Diseases and pests.*—*Cleome hassleriana* is known to be generally free of disease and pest problems and no problems to either diseases or pests has been observed for the new cultivar, because there are no known causative agents known to be a problem for *Cleome*, no resistance to a particular agent can be claimed.

*Root description.*—Fibrous, 155A.

*Propagation type.*—Stem cuttings and tissue culture.

*Root development.*—Roots initiate in 2 to 3 weeks, rooted stem cuttings will fully root as a young plant in 4 to 6 weeks.

*Growth rate.*—Moderate.

Stem description:

*Stem shape.*—Round.

*Stem color.*—145A, tinged at base and top 183A.

*Stem size.*—Average of 27 cm in length and 5 mm in diameter.

*Stem surface.*—Densely covered with very short stiff hairs; average of 0.5 mm in length and NN155D in color.

*Stem strength.*—Sturdy, strong.

*Stem aspect.*—Held upright nearly vertical.

*Internode length.*—Average of 1 cm.

*Branching habit.*—Stems arise from base, an average of 1 to 2 branches.

Foliage description:

*Arrangement.*—Alternate; palmately compound with seven leaflets per leaf (occasionally 5).

*Fragrance.*—None detected.

*Leaf size.*—Whole leaf size; average of 10 cm in length, 9 cm in length.

*Leaflet size.*—Center leaflet; 6.5 cm in length and 2 cm in width, lateral leaflets; 5 cm in length and 1.5 cm in width, lower leaflets; 2.5 cm in length and 1 cm in width.

*Leaflet shape.*—Elliptical.

*Leaflet apex.*—Acute.

*Leaflet base.*—Attenuate.

*Leaflet margin.*—Entire.

*Leaflet texture.*—Both surfaces dull and rough to the touch, covered with minute stiff pubescence.

*Leaflet spine.*—Average of 3 mm in length, very thin and linear in shape, 155B in color, glabrous surface.

*Leaflet attachment.*—Sessile.

*Leaf venation.*—Pinnate.

*Leaf color.*—Young leaflets upper and lower surface; slightly variegated with centers N144A and 143A and margins 141A and lightly flushed with 79D, mature leaflets upper and lower surface; variegated with centers 145A to 145B and margins 155A, tinged with 79C at the leaf attachment.

Flower description:

*Inflorescence type.*—Single flowers arranged in short terminal racemes.

*Inflorescence size.*—An average of 4 cm in height and 5 cm in width.

*Fragrance.*—None detected.

*Flower lastingness.*—Single flowers last an average of 1 week.

*Flower buds.*—Average of 1.5 cm in length, 4 mm in diameter, linear in shape, color a blend of NN78A and N77A at the tip.

*Flower size.*—An average of 3 cm in depth and width.

*Petals.*—4, in a single whorl, average of 2 cm in length, 1 cm in width, elliptical in shape, broadly acute apex, attenuate base, entire margins, upper and lower surface texture is smooth, glabrous and velvety, color when opening upper and lower surface; a blend of 71A and 76C, margins 76C, base 72A, color when fully open upper and lower surface; NN78A, light overlay of 79C in the middle, 77B and 79A at base, veins N74A, upper and lower surface fading to N75A at tips to mid section and 75C at petal base and margins.

*Sepals.*—5, in a single whorl, average of 2 mm in length, 0.5 mm in width, lanceolate. in shape, acute apex, truncate base, entire margins, upper and lower surface texture is glabrous, both surfaces 79A in color.

*Peduncles.*—Average of 2 cm in length, 1 mm in width, surface is moderately pubescent, slightly glossy, 142A to 142C, flushed with N77A towards the top.

*Flower bracts.*—4, in a single whorl, average of 9 mm in length, 2 mm in width, lanceolate in shape, acute apex, truncate base, entire margins, upper and lower surface texture is smooth, margins densely covered with minute hairs, both surfaces 11C in color.

Reproductive organs:

*Gynoecium.*—Pistil; 1, up to 5 cm in length, long and extended, stigma; round, N79A in color 1 mm in diameter, style; 2.8 cm in length, a blend of 83A and 61A in color, ovary; 2 mm in length, 1 mm in diameter, 145B in color.

*Androecium.*—Stamens; 6, filament; 5 cm in length, 0.5 mm in width, NN78A in color anther; linear, 79A in color, 5 mm in length, 0.5 mm in width, pollen; moderate in quantity, 164A in color.

*Fruit.*—Average of 5 cm in length, 3 mm in diameter, linear in shape, slightly glossy and glabrous surface, a blend of 160A and 146A in color.

*Seeds.*—Average of 50, circular and spiral in shape, average of 2 mm in diameter, glossy and glabrous, 145B in color.

It is claimed:

1. A new and distinct variety of *Cleome* plant named 'Creme de la Creme' as described and illustrated herein.

* * * * *